United States Patent [19]

Hvid

[11] Patent Number: Plant 6,180

[45] Date of Patent: May 17, 1988

[54] BEGONIA PLANT NAMED INA

[75] Inventor: Soeren Hvid, Aarup, Denmark

[73] Assignee: L. Daehnfeldt A/S, Odense, Denmark

[21] Appl. No.: 838,078

[22] Filed: Mar. 10, 1986

[51] Int. Cl.[4] ..... A01H 5/00

[52] U.S. Cl. ..... Plt./68

[58] Field of Search ..... Plt./68

*Primary Examiner*—Robert E. Bagwill

*Attorney, Agent, or Firm*—Olson and Olson

[57] ABSTRACT

A new and distinctive cultivar of begonia plant with a vigorous, compact growth habit, almost white tepals that fade into very light pink, a floriferous display and benefits by its excellent keeping qualities.

1 Drawing Sheet

BACKGROUND OF THE INVENTION

This invention relates to a new and distinctive cultivar of begonia plant known botanically as *Begonia hiemalis* Begonia (Fotsch) and known by the cultivar name Ina.

This new cultivar was discovered by me as a mutation of Barbara observed in a group of plants.

Asexual reproduction by stem and/or leaf cuttings has reproduced the unique features of the new cultivar through successive propagations.

The following characteristics distinguish the new begonia from both its parents and other begonias commercially known and used in the floriculture industry:

(1) The new cultivar shows pubscense on the foliage. The plant form is vigorous and compact.

(2) In comparison to Barbara, which has pink double flowers, the flower color of Ina is much more light pink and the bud is almost white.

(3) In all other respects the mutation has nearly the same morphological appearance as the parent excepting the lighter flowers and the white buds.

(4) The new cultivar is considered to be floriferous. The stems on which flowering occurs tend to have initiation and development at several nodes at one time.

(5) The keeping qualities of the flowers and the foliage in all seasons allows production and sales efficiencies to be maximized.

(6) The new cultivar tends to be very vigorous so that 10 cm. pot production is best done with shoot cuttings and tip pinching.

(7) Propagation by leaf cuttings is difficult under light and high temperatures in summer months. Stem cuttings can readily be produced in this season.

(8) The flowers of Ina undergo little or no fading under abnormal conditions. Ina is also very superior with respect to keeping qualities of winter crops of hiemalis begonias.

THE DRAWING

The accompanying color photograph illustrates the overall appearance of this cultivar taken as a face view of the plant and showing the colors as true as it is reasonably possible to obtain in a colored reproduction of this type.

DESCRIPTION OF THE NEW VARIETY

The following is a detailed description of my new begonia cultivar based on plants produced under commercial practices in glasshouses in various places in Denmark. Color references are made to The Royal Horticultural Society Colour Chart, except where general color terms of ordinary dictionary significance are used.

Parentage:

A mutation of the cultivar Barbara.

Propagation:

*Type cutting.*—Stem cutting.

*Time to root.*—27–30 days at 21° C. in summer; 25–28 days at 21° C. in winter.

*Rooting habit.*—Uniform, dentritic, fibrous.

THE PLANT

Form: Low bush type, self-branching, herbaceous.

Habit of growth: Generally rapid, vigorous with strong stems, strong penduncles and strong pedicles.

Foliage: Leaves simple, alternate, borne on vigorous petioles, firm.

(1) *Size.*—Average leaf at maturity from 7–9 cm. (2.75–3.54 inches) leaves may be larger or smaller depending on density of leaf canopy.

(2) *Shape.*—Ovte, slightly concave.

(3) *Texture.*—Leaf is firm, top glabrous, underside rugose.

(4) *Margin.*—Crenate.

(5) *Color.*—young foliage top side; green, under side; yellow green, mature foliage top side; yellow green to green, under side; yellow green.

(6) *Veination.*—Palmate.

THE FLOWER

Flowering habits: Flowering in racemes, with several clusters arising from the stem nodes at the same time giving a highly floriferous appearance. Flowering is continuous for a long period of time.

Natural flowering season: Flowering occurs naturally with shortened days lengths beginning mid-September and continuing through May. Reducing day length in summer speeds up flower initiation.

Flower bud: Flat, oval, nearly round, and almost white flower buds.

Flowers borne: On vigorous penduncles and pedicles in a raceme. The extra doubleness of the flowers causes a pendulous appearance because of the weight of the flowers.

Quantity: Very floriferous, often having 18–20 flowers per main stem in flowering stage at one time.

Tepals:

(1) *Shape.*—Nearly circular.

(2) *Color.*—Top side in winter when opening: very light pink HCC 622/1. fading to: light pink HCC 621/1. under side: light pink HCC 621/1.

(3) *Number.*—16–32.

(4) *Size.*—Basal from 25 mm (1.0 inch), interior tepals 10–20 mm (0.4–0.8 inch).

(5) *Flower size.*—Up to 5 cm (2 inches).

Reproductive organs:

*Stamens.*—None; cultivar is sterile.

Disease resistance:

No particular increase in resistance to disease observed to date.

I claim:

1. A new and distinct cultivar of *Begonia hiemalis* plant named Ina, as shown and described, and particularly characterized by its vigorous, compact growth habit, almost white tepals that fade into very light pink; floriferous habit and by its excellent keeping qualities.

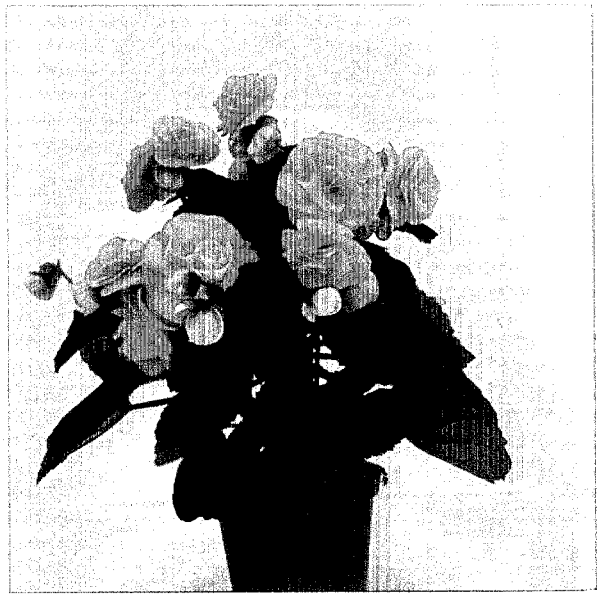

* * * * *